United States Patent [19]

Duch

[11] 4,034,870
[45] July 12, 1977

[54] DEVICE FOR INTRODUCING A SUBSTANCE, PARTICULARLY A PULVERULENT SUBSTANCE, FROM A CHAMBER HAVING A PRESSURE P1, INTO A CHAMBER HAVING A PRESSURE P2 HIGHER THAN P1

[76] Inventor: Bernard P. Duch, 201 Rue Saint-Denis, Colombes (Haute de Seine), France

[21] Appl. No.: 577,888

[22] Filed: May 15, 1975

[30] Foreign Application Priority Data

May 15, 1974 France .................. 74.16886
May 6, 1975 France .................. 75.14200

[51] Int. Cl.² ........................ B65G 65/30
[52] U.S. Cl. .................... 214/17 CB; 137/56; 198/642; 233/20 A; 302/11; 302/38
[58] Field of Search .............. 302/32, 38, 49, 52, 302/53, 11–13; 222/410; 233/20 A, 20 R; 137/56; 198/128, 642; 214/17 CB; 414/217

[56] References Cited

U.S. PATENT DOCUMENTS

| | | | |
|---|---|---|---|
| 1,585,393 | 5/1926 | Laughlin | 233/20 A |
| 1,640,707 | 8/1927 | Laughlin | 233/20 R |
| 2,822,097 | 2/1958 | Lee | 198/128 |
| 2,920,793 | 1/1960 | Munsell | 222/410 |
| 3,151,784 | 10/1964 | Tailor | 302/49 UX |
| 3,182,825 | 5/1965 | Zellerhoff | 222/410 |
| 3,240,533 | 3/1966 | Mommsen | 302/49 |

*Primary Examiner*—Johnny D. Cherry
*Assistant Examiner*—Jeffrey V. Nase
*Attorney, Agent, or Firm*—Young & Thompson

[57] ABSTRACT

The present invention comprises a device which allows to introduce a substance from a chamber A, having a pressure P1, into a chamber B, having a pressure P2 higher than P1, said device comprising a stator, in which the pressure is that of the chamber B and in which rotates a rotor formed by a chamber V at the pressure P1, said rotor comprising a central opening through which is introduced the product coming from the chamber A, and a peripheral slot adapted to be opened, under the thrust produced by the material collected in the rotor chamber V and subjected to centrifugal force, in order to let said material run through the slot, into the stator.

2 Claims, 2 Drawing Figures

DEVICE FOR INTRODUCING A SUBSTANCE, PARTICULARLY A PULVERULENT SUBSTANCE, FROM A CHAMBER HAVING A PRESSURE P1, INTO A CHAMBER HAVING A PRESSURE P2 HIGHER THAN P1

BACKGROUND OF THE INVENTION

1. Field of the Invention

The present invention relates to a device allowing one to introduce a product, particularly a pulverulent product, from a chamber A having a pressure P1, into a chamber B having a pressure P2 higher than P1.

According to one of the most widely known techniques, devices of this type are designed to introduce a pulverulent product — which is at ambient pressure — into a conduit under pressure, which provides for the pneumatic conveyance thereof; for this purpose, a gaseous flow runs through the conduit at such a pressure and speed that it is capable of carrying along the solid product to be conveyed, from a starting point X towards an arrival point Y. For this purpose, a pump keeps between the points X and Y a pressure difference equal to the pressure losses produced by the circulation, at the intended speed, of a mixture of the gas and the product being conveyed.

Gaseous flow pumps do not however allow the passage of solid materials, other than in minimum proportions in respect of the volume of the pumped fluid. Consequently, one is inclined to place said pump, either upstream of the point of introduction of the product, or downstream of the collection point of the product, that is, either before the poing X, or after the point Y.

It is hence necessary to use a device allowing one to introduce the product into the conduit under pressure between the points X and Y, said device being generally called an introducer: such introducers are at present known and on the market, in various types of constructions.

2. Description of the Prior Art

A first known construction consists of passage tanks, which are alternatively brought to room pressure, to be filled with material, and subsequently to the pressure of the conduit to allow the passage of the material towards the latter. However, these tanks have necessarily the drawback of being scarcely safe, due to their complex structure, besides being very costly and notably bulky.

A further construction consists of rotary gates, having the advantage that they work continuously: they are extremely simple and safe, but they do not allow one to exceed pressure differences higher than 600 millibars. They have no abrasion resistance and they usually have considerable gas leaks.

A still further construction of introducers of solid substances into a gaseous flow, consists of a worm screw device having non-constant pitch. Such device, which is highly simple and safe, has the drawback of using too much energy, of being limited to a pressure difference of about 2 bars, of having a poor resistance to abrasion, and finally, of being unemployable for fragile or thermosensitive products, the compression and temperature increase of the product in the last turn of the screw being actually considerable.

There are also continuous pneumatic elevators, consisting of a tank inside which the product to be conveyed is fluidified over a height equal to the back-pressure which should be obtained. Elevators of this type are particularly interesting for the numerous practical advantages which they provide, in particular: great safety in working, low energy consumption with low power, very good abrasion resistance, and continuous working. However, the drawback of such a device lies in the remarkable height which is normally required for the tank in which the product is fluidified: in fact, with a product having a specific gravity of about 1, it is necessary to use a tank having a height of about 10 m. in order to obtain a pressure difference of 1 bar.

SUMMARY OF THE INVENTION

The object of the present invention is to eliminate the drawbacks of known devices and to create an introducer of modest dimensions, which allows to work with a high pressure difference and which does not have the inconvenience of being limited, like the pneumatic elevators, by the specific weight of the product to be introduced.

For this purpose, the invention is a device which allows one to introduce a substance from a chamber A, having a pressure P1, into a chamber B, having a pressure P2 higher than P1, characterized in that it comprises a stator, in which th pressure is that of the chamber B and in which rotates a rotor formed by a chamber V at the pressure P1, said rotor comprising a central opening through which is introduced the product coming from the chamber A, and a peripheral slot adapted to be opened, under the thrust produced by the material collected in the rotor chamber V and subjected to centrifugal force, in order to let said material run through the slot, into the stator.

In this way, the pressure difference P2 − P1 may be established to the desired value, it being always possible to introduce the substance into the chamber B, provided that the thrust of the product against the inner walls of the rotor, produced by th centrifugal force acting on the product itself, is sufficiently higher than the pressure existing in B.

Moreover, the pressure existing in centrifuged product is in no way bound to kinetic energy, and the flowing speed of the product inside the rotor may be reduced to the desired value: consequently, the power lost due to impact friction is negligible; it is further possible to treat fragile products, abrasion is highly reduced, and the flow can be regulated in a continuous way.

BRIEF DESCRIPTION OF THE DRAWINGS

Further characteristics and advantages of the device according to the present invention will be described in more detail in the following description, with reference to some preferred embodiments of the device itself, illustrated in the accompanying drawings, in which.

DESCRIPTION OF THE PREFERRED EMBODIMENTS

Figure 1:
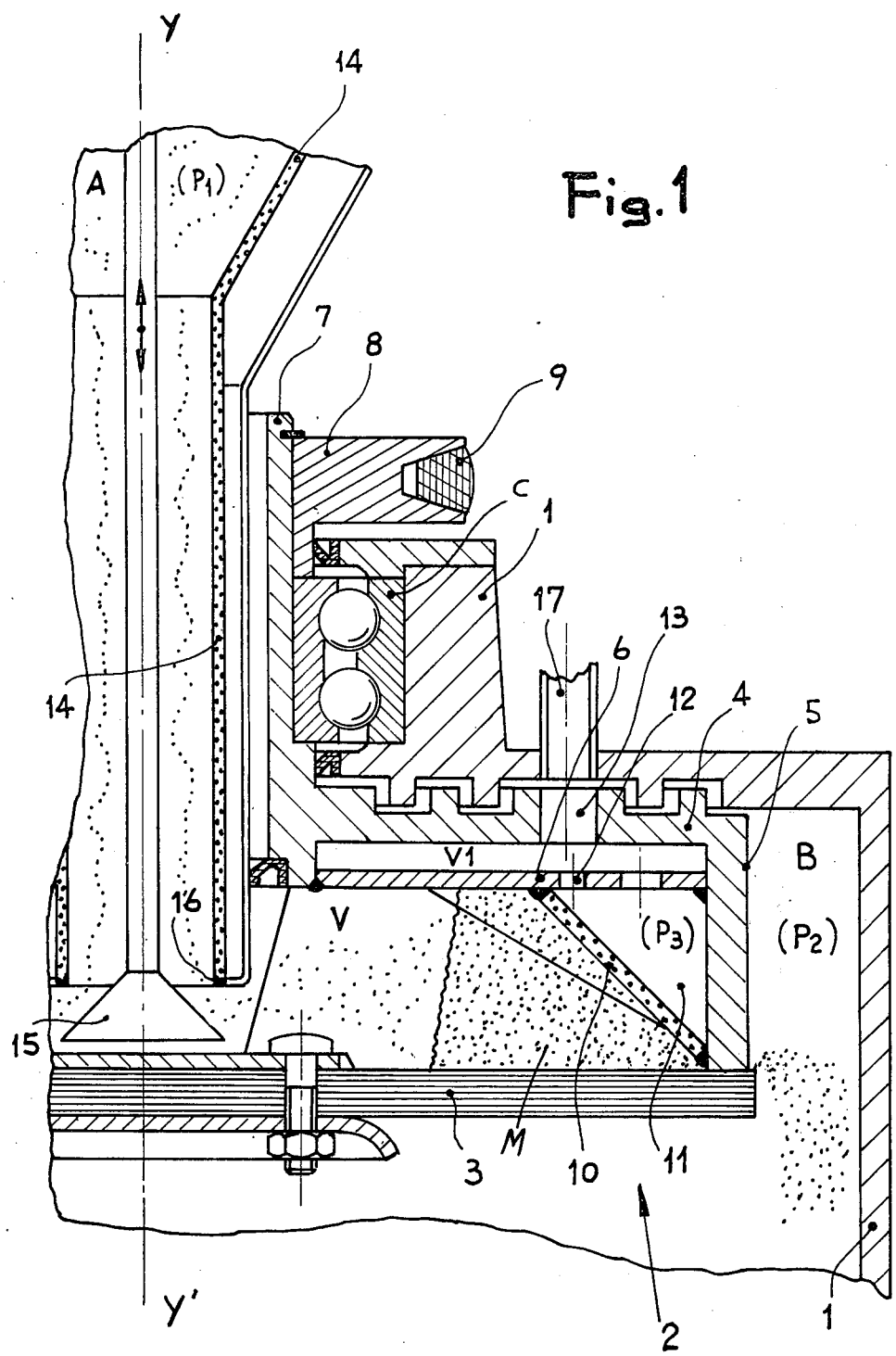
FIG. 1 is a schematic view, partially in axial section, of a first embodiment of the device.

As shown in FIG. 1, the device allowing to introduce the product from a chamber A having a pressure P1, into the chamber B having a pressure P2 higher than P1, comprises a stator 1, which bounds the chamber B and in which rotates a rotor 2, around vertical axis Y—Y'.

Said rotor comprises an essentially cylindrical body, delimitied by two base walls 3 and 4, respectively the lower and upper wall, and by a side wall 5. Below and at a short distance from the upper wall 4, is fixed an annular rigid disk 6, which separates the main volume V of the rotor, from a small secondary chamber with volume V1.

The lower wall 3 is formed by a disk of material capable of bending fixedly anchored at the centre and with the peripheral portion bearing against the lower edge of the wall 5.

Said bearing — assured, on one hand, by the flexibility of the disk 3, and on the other hand, by the thrust produced by the pressure P2 existing in B, and higher than the pressure P1 existing in volume V — provides a perfect seal.

The walls 3, 4, 5 and 6, forming the rotor, are mounted on the hollow shaft 7, which is in turn rotatably mounted on the stator 1, by means of a guiding and rolling member C, consisting for example of a double-row ball bearing. A driving pulley 8, integral with the hollow shaft 7, is caused to rotate by a motor (not shown) by means of the belt 9, and causes in turn the rotation of the rotor 2.

Between the upper annular disk 6 and the base of the wall 5, is fixed a conical wall 10 comprising a plurality of perforations. The revolution volume 11 of triangular section, which is formed between the conical wall 10 and the walls 5, 6, is connected, through openings 12, with the volume V1 of the secondary chamber formed between the wall 4 and the annular disk 6. Through passages 13 of the same wall 4, the volume V1 is fed with gaseous fluid at a pressure P3 (higher than P2), through the nozzle 17.

The substance to be conveyed is introduced through the feed pipe 14, of cylindrical section, which is fixed and arranged inside the hollow shaft 7. The amount of material being fed is regulated by means of the conical valve 15, by drawing the latter more or less close to the lower edge 16 of the pipe 14.

The material introduced, drops onto the base wall 3 of the rotor 2, and the centrifugal force piles up the material into a ring M at the periphery of the revolution volume V. The thrust of the material increases with the increase of the mass of the ring M; when said thrust exceeds the flexural strength of the wall 3, the latter bends, opening a peripheral passage through which the material escapes towards the stator. For this purpose, it is evident that the thrust produced by the material should be higher than the sum of the actual flexural strength of the wall 3, and of the pressure P2 acting on the outer face of the wall 3 itself.

Upon opening of said peripheral passage of the rotor, the material starts to run through said passage towards the stator, hence passing from the chamber with pressure P1, towards the chamber with higher pressure P2.

The running of the material through said passage is facilitated by the fact that the gas with pressure P3 flows from the chamber 11 through the perforated wall 10 and through the material of the ring M, said material being hence at least partially fluidified.

Figure 2:
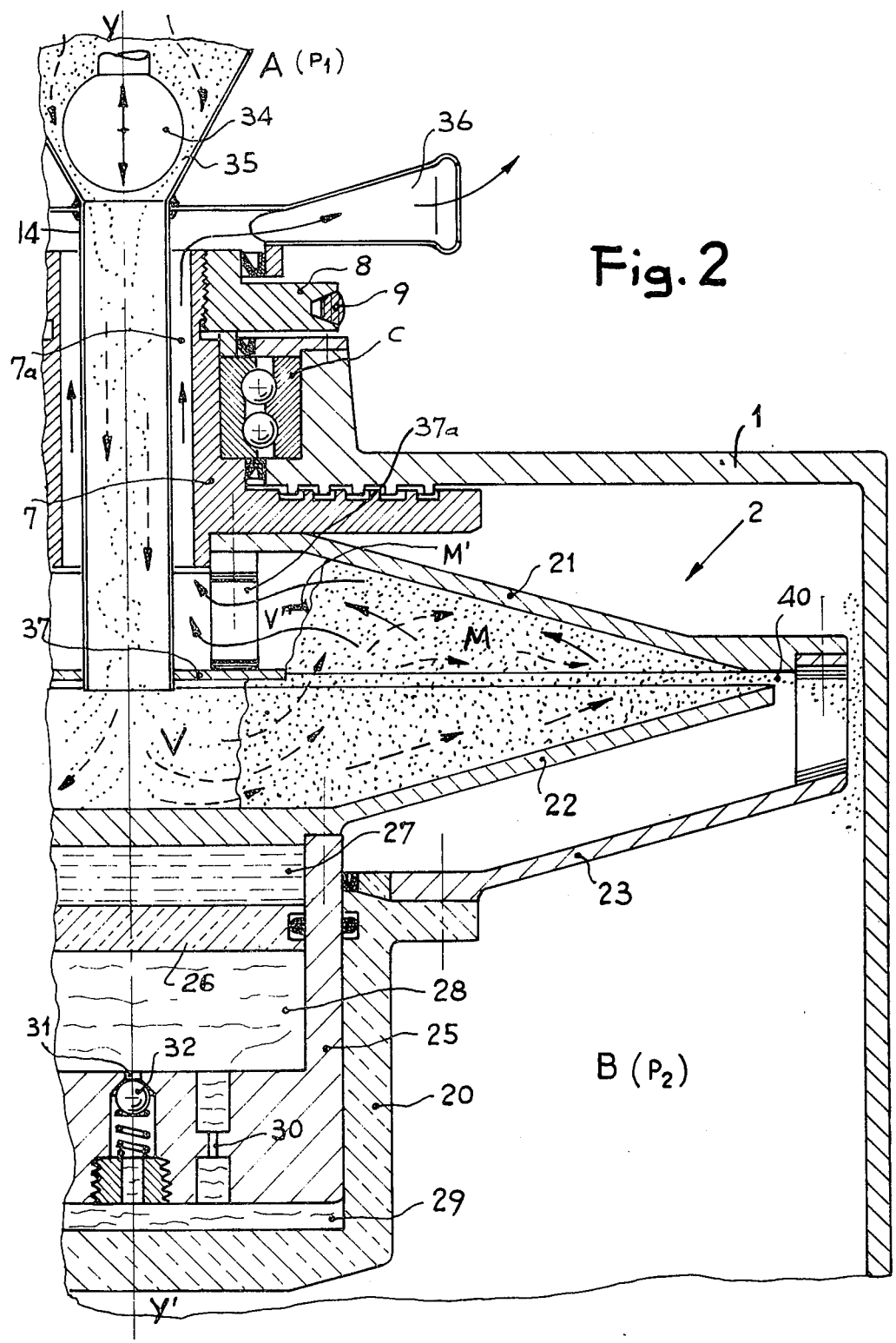
FIG. 2 is a similar axial section view, of a further embodiment.

The embodiment of FIG. 2, like that shown in FIG. 1, comprises a stator 1, in which rotates a rotor 2, to which latter is connected a feed pipe 14, which is stationary. The chamber V, being formed in the rotor 2, and the feed pipe 14 are kept at the pressure P1, while the chamber B of the stator 1 is kept at the pressure P2 higher than P1.

Unlike the rotor with an essentially cylindrical structure, according to the embodiment of FIG. 1, the rotor comprises, in this case, two half cups 21 and 22, shaped like a very open cone. The half cup 21 is integral with the hollow shaft 7, by which it is caused to rotate.

To the peripheral edge of the half cup 21 is fixed a downwardly projecting cage 23, which supports a cylinder unit 20, incorporating an elastic thrust system and a dampening system, both of which will be better described hereinafter.

More precisely, inside the cylinder 20 is mounted the secondary cylinder 25, axially sliding along the rotation axis Y—Y' of the rotor and to the top of which is fixed the half cup 22.

Inside the secondary cylinder 25 is moreover slidably mounted a piston 26, which separates the inner cavity of the cylinder 25 into two chambers 27 and 28. A further chamber 29 is formed between the cylinder 25 and the cylinder 20.

The chamber 27 contains a gas under pressure, preferably nitrogen.

The chamber 28 is connected with the chamber 29 of the cylinder 20, beyond the head of the secondary cylinder 25, through a very narrow passage 30, as well as through a further wider passage 31 being which is closed by a check valve 32.

As already seen hereabove, the shaft 7 is caused to rotate by a pulley 8 integral therewith and operated by a belt 9, said shaft being supported by a bearing C.

The feed pipe 14 ends at its top in a conical charging hopper, with which is associated a ball valve 34, which bears against the seat 35 of the hopper, and through which it is possible to control the feeding.

With the stationary feed pipe 14 is finally associated an upper discharge nozzle 36, which is internally connected with a passage 7a, formed between the pipe 14 and the inner cavity of the shaft 7.

The operation of this embodiment is substantially like that of the embodiment according to FIG. 1: once the rotor 2 — with the two half cups in mutual sealed contact — is set rotating, one starts to introduce the pulverulent material from the top of the pipe 14.

The material falling into the rotor 2 is at once conveyed towards the periphery, owing to the centrifugal force. It forms a ring M of material, the mass of which gradually increases, thereby increasing also the thrust produced by said material on the inner walls of the rotor.

When the thrust on said walls, and in particular against the inner wall of the half cup 22, has reached a sufficient value — namely, a value exceeding the thrust which the pressure P2 produces on the outer wall of the actual half cup 22, plus the upward thrust produced by the gas under pressure contained inside the chamber 27 — the half cup 22 starts moving downward.

Said downward movement is very slow, in that it is controlled by the dampening system formed by the fluid contained in the chambers 28 and 29, which fluid — upon the descent of the cylinder 25, under the pressure of the half cup 22 — passes very slowly through the narrow passage 30, so as to move from the chamber 29 to the chamber 28.

As soon as the half cup 22 has slightly moved apart from the half cup 21, the pulverulent material starts running through the peripheral opening 40, towards the chamber B having a pressure P2. If the amount of material running through the passage 40 is equal to the amount of material being fed through the pipe 14, the opening movement of the half cup 22 ceases, and conditions of equilibrium are established, in which there is a regular passage of material from the chamber V having a pressure P1, towards the chamber B having a pressure P2.

A certain amount of air will filter, in countercurrent, through the same passage 40, into the chamber V, and from here it is discharged through the channel 7a and the nozzle 36. The above, and the fact that the passage of the material through the rotor, towards the chamber B, takes place in a regular and uniform way, prove that — even without providing for an appropriate fluidifying system, as in the embodiment of FIG. 1 — the device of FIG. 2 likewise carries out an at least partial fluidifying action on the material contained in the rotor.

When the feeding of the material stops, the ring mass at the periphery of the rotor is quickly reduced, so that the thrust of the pressure P2 outwardly of the half cup 22 and the thrust produced by the gas under pressure in the chamber 27, cause the rising of the half cup 22 and the closing of the rotor. Said rising takes place rapidly, thanks to the opening of the valve 32.

According to the present invention, a particular expedient has been worked out, in order to obtain the forming of a certain free volume, at the centre of the rotor, which is adapted to collect the air which filters in countercurrent from the chamber B, through the fluidified material, so as to allow the proper discharge of said air towards the nozzle 36. Said expedient consists in providing an annular disk 37, which rings the outlet of the pipe 14 inside the rotor and which is fixed to the half cup 21 by means of a cage 37a, the latter allowing the free passage of air, as indicated by the arrows on the drawing.

Thanks to the use of the disk 37, the material being fed under said disk settles according to the slope M', leaving free the volume V" around the base of the outlet channel 7a.

The device according to the present invention has exhibited — in the practical tests which have been carried out — a perfectly equilibrated and regular operating particularly sensitive and responsive to pressure variations in the chamber of the stator.

It has specifically been found that, as a result of pressure increases in the conveyance conduit — for example, due to cloggings in said conduit — the higher pressure acting from the outside on the wall of the half cup 22, causes the immediate closing of the rotor, hence facilitating the fast elimination of the clogging.

It is to be understood that the invention is not limited to the embodiments described and illustrated, but that there may be many modifications thereof, without thereby departing from the scope of the invention itself.

In particular, it has been suggested herein to use the device according to the invention for introducing material, especially pulverulent material, from a chamber with atmospheric pressure, into an air conduit with higher pressure. This, however, is not to be considered in a limitative sense, but merely by way of example, since the device according to the present invention may be used in all those cases in which it is necessary to transfer material from a first chamber, having a given fluid pressure — even liquid — to a second chamber, having a higher fluid pressure. For example, the device according to the invention may be used, not only for the pneumatic or hydraulic conveyance of material, but also in chemical processes, for introducing material in reaction chambers having a pressure higher than ambient pressure, hence making it possible to carry out continuous reactions in all those cases wherein, to date, one was forced to carry out discontinuous reactions.

I claim:

1. Apparatus for the introduction of a substance from a space under relatively low pressure to a space under higher pressure, comprising a stator which defines said space under higher pressure, a rotor that rotates within said stator and that defines said space under relatively low pressure, means to introduce said substance into said rotor, said rotor being formed in two parts that contact each other along a peripheral line, means mounting said two parts for movement of at least one of said parts away from the other of said parts in a direction parallel to the axis of rotation of the rotor, said rotor having a rigid perforated wall therein, on one side of which said material collects upon rotation of said rotor, and means for passing through said rigid wall a gas under a pressure higher than said higher pressure thereby to fluidify the material in the rotor.

2. Apparatus as claimed in claim 1, said wall being frusto-conical and tapering outwardly toward said peripheral line.

* * * * *